US00PP27304P2

(12) United States Plant Patent
Berry

(10) Patent No.: US PP27,304 P2
(45) Date of Patent: Oct. 25, 2016

(54) ***HIBISCUS* PLANT NAMED 'JBN 12002'**

(50) Latin Name: *Hibiscus rosa-sinensis*
Varietal Denomination: JBN 12002

(71) Applicant: James B. Berry, Mineola, TX (US)

(72) Inventor: James B. Berry, Mineola, TX (US)

(73) Assignee: CAPSTONE PLANTS, INC., Grand Saline, TX (US)

( * ) Notice: Subject to any disclaimer, the term of this patent is extended or adjusted under 35 U.S.C. 154(b) by 8 days.

(21) Appl. No.: 14/545,308

(22) Filed: Apr. 21, 2015

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hibiscus* named 'JBN 12002', that is characterized by its well branched plant habit, its large flowers that are deep red in color, its floriferous blooming habit, its glossy green foliage, its vigorous growth habit, and its foliage that is resistant to dieback disease and leaf spot.

2 Drawing Sheets

Botanical classification: *Hibiscus rosa-sinensis.*
Cultivar designation: 'JBN 12002'.

BACKGROUND OF THE INVENTION

The present invention relates to a new and distinct cultivar of *Hibiscus rosa-sinensis* named 'JBN 12002' and will be referred to hereafter by its cultivar name, 'JBN 12002'. 'JBN 12002' is a new cultivar of tropical *hibiscus* grown for use as a landscape and container plant.

The new cultivar was developed through an ongoing breeding program conducted by the Inventor in Grand Saline, Tex. The objectives of the breeding program are to develop new cultivars of *Hibiscus* that exhibit increased disease resistance, glossy foliage, large uniquely colored flowers, a floriferous blooming habit and a well-branched plant habit.

'JBN 12002' arose from a cross made by the Inventor in March of 2011 between the *Hibiscus rosa-sinensis* 'Kiss and Tell' (not patented) as the female parent and *Hibiscus rosa-sinensis* 'Little Red' (not patented) as the male parent. 'JBN 12002' was selected as a single unique plant from the resulting seedlings in January of 2012.

Asexual propagation of the new cultivar was first accomplished by stem cuttings in Grande Saline, Tex. in February of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'JBN 12002' as a new and distinct cultivar of *Hibiscus.*

1. 'JBN 12002' exhibits a well branched plant habit.
2. 'JBN 12002' exhibits large flowers that are deep red in color.
3. 'JBN 12002' exhibits a floriferous bloom habit.

4. 'JBN 12002' exhibits glossy green foliage.
5. 'JBN 12002' exhibits a vigorous growth habit.
6. 'JBN 12002' exhibits foliage that is resistant to dieback disease and leaf spot.

The female parent of 'JBN 12002', 'Kiss and Tell', differs from 'JBN 12002' in having multicolored flowers that are larger in size. The male parent of 'JBN 12002', 'Little Red', differs from 'JBN 12002' in having flowers and leaves that are much smaller in size. 'JBN 12002' can be most closely compared to the *Hibiscus* cultivar and 'Roller Coaster' (not patented). 'Roller Coaster' is similar to 'JBN 12002' in having a floriferous blooming habit and in being well branched. 'Roller Coaster' differs from 'JBN 12002' in having flowers that are multicolored and in having leaves with a textured surface.

BRIEF DESCRIPTION OF THE DRAWINGS

The accompanying colored photographs illustrate the overall appearance and distinct characteristics of the new *Hibiscus*. The photographs were taken of seven month-old plants of 'JBN 12002' as grown in a one-gallon container in a greenhouse in Grand Saline, Tex.

The photograph in FIG. 1 provides a side-view of three plants of 'JBN 12002' in bloom.

Figure 1:
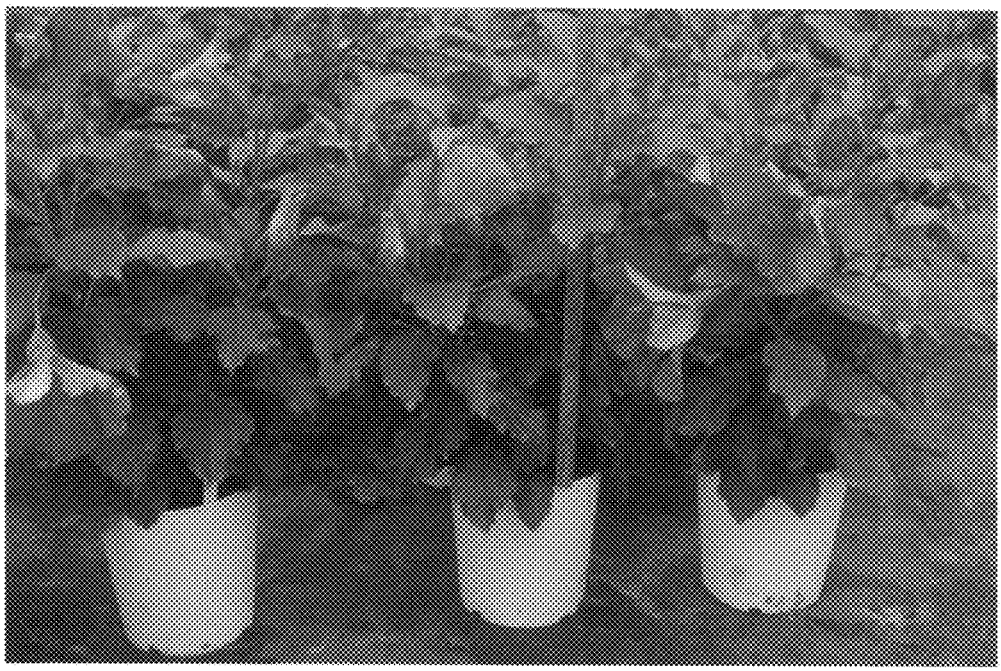
Figure 2:
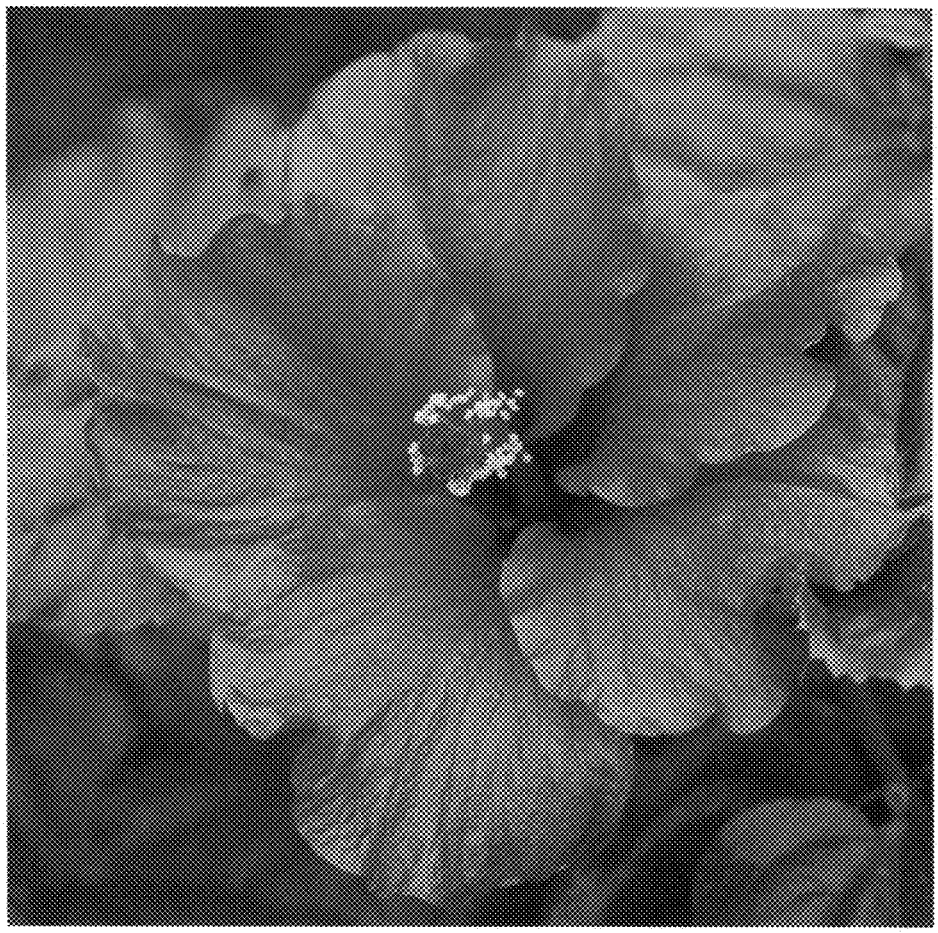

The photograph in FIG. 2 provides a close-up view of a flower of 'JBN 12002'.

The colors in the photographs are as close as possible with the photographic and printing technology utilized and the color values cited in the Detailed Botanical Description accurately describe the colors of the new *Hibiscus.*

DETAILED BOTANICAL DESCRIPTION OF THE PLANT

The following is a detailed description of 7 month-old plants of the new cultivar as grown in one-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Continuously in warm temperatures in Grand Saline, Tex.

*Plant type*.—Tropical evergreen shrub.

*Plant habit*.—Upright and well branched.

*Height and spread*.—An average of 45 m in height and 33 cm in spread as grown in a one gallon container and reaches an average of 2.1 m in height and 1.5 cm in spread when mature in the landscape.

*Hardiness*.—Tropical; at least in U.S.D.A. Zones 9 to 11.

*Diseases*.—Resistance to dieback disease (*Erwinia* spp.) and leaf spot (*Cerospora* spp.) has been observed.

*Root description*.—Fibrous roots.

*Propagation*.—Stem cutting.

*Growth rate*.—Vigorous.

Stem description:

*Shape*.—Slightly oval.

*Stem color*.—New growth; 144A, mature wood; 191A with striations of 138A.

*Stem size*.—An average of 32 cm in length and 5 mm in width.

*Stem surface*.—New growth; Glabrous, maturing wood; very sparse hairs, mature wood; finely striated.

*Stem aspect*.—Held upright to an average angle of 10° (0°=vertical).

*Stem strength*.—Strong.

*Branching*.—Heavy basal branching; an average of 8 in a one-gallon container.

*Internode*.—Average of 2 cm.

*Stipules*.—1 to 2 per leaf node, linear to narrowly lanceolate in shape, an average of 9 mm in length and 1 mm in width, glabrous surface, acuminate apex, truncate base, 138B in color.

Foliage description:

*Leaf shape*.—Ovate.

*Leaf division*.—Simple.

*Leaf base*.—Rounded.

*Leaf apex*.—Acute.

*Leaf venation*.—Pinnate, 138A on upper surface and 138B on lower surface.

*Leaf margins*.—Serrate and wavy, tips of serration have a small mucronate tip.

*Leaf attachment*.—Petiolate.

*Leaf arrangement*.—Alternate.

*Leaf orientation*.—Primarily horizontal to petiole.

*Leaf aspect*.—Primarily flat with wavy margins.

*Leaf surface*.—Upper surface glabrous and glossy, lower surface very finely puberulent and satiny.

*Leaf color*.—Young and mature leaves upper surface N137A, lower surface 138A.

*Leaf size*.—An average of 10 cm in length, and 8.5 cm in width when mature.

*Leaf quantity*.—An average of 11 leaves per stem 32 cm in length.

*Petioles*.—An average of 4.0 cm in length and 2.5 mm in diameter, 138A in color and 144A near leaf blade, finely pubescent surface with a center ridge on upper surface.

Flower description:

*Inflorescence type*.—Flowers are solitary from upper leaf axils.

*Lastingness of flowers*.—About 1 day, self cleaning.

*Flower size*.—An average of 8.5 cm in depth and 13.5 cm in diameter.

*Flower fragrance*.—None.

*Flower shape*.—Rotate.

*Flower number*.—An average of 4 flowers and buds present per stem at one time, continuously produces throughout the summer.

*Flower aspect*.—Outward when fully open to slightly pendulous.

*Flower bud*.—Elliptic in shape, an average of 5 cm in length and 2 cm in width, color a blend of 45B and 4C with very apex suffused with N77C (petal portion), sepal portion a blend of 144A and 144B.

*Flower attachment*.—Peduncle.

*Petals*.—5, un-fused, overlapping, oblanceolate in shape, an average of 9.5 cm in length and 5.5 cm in width, serrate and wavy margins, rounded apex, base is cuneate slightly oblique and adnate to base of style slightly recurved, lower surface is satiny and waxy, upper surface is glabrous and waxy near the base (throat), color of upper surface is a blend of 45A, 45B, and 45C and blending to 46C at the base (throat), color lower surface is a blend of 46B and 45B that blends with 55A near base and one side (2 cm towards edge) is flushed with 4C and veins are 4C or 55A.

*Calyx*.—Campanulate in shape, average of 3 cm in length and 2.5 cm in diameter.

*Epicalyx*.—An average of 2 cm in length and 4 mm in width, sparsely pubescent surface, color a blend of 144A and 144B.

*Sepals*.—4, base 50% fused, an average of 3 cm in length and 1.2 cm in width, color of both surfaces is a blend of 144A and 144B, outer surface is puberulent and inner surface is glossy, acute apex.

*Peduncles*.—An average of 6 cm in length and 2 mm in diameter, moderate strength, average angle is downward at 45°, 144A to 144B in color, glabrous surface.

*Pedicels*.—Not present, flowers are solitary from terminal leaf axils.

*Bracts*.—5, bracts held upright surrounding sepals, lanceolate in shape, apiculate apex, truncate base, average of 1.5 cm in length and 4 mm in width, color of both surfaces is 137C and 144A near base, both surfaces are glabrous.

Reproductive organs:

*Gynoecium*.—1 pistil, about 8.5 cm in length, stigmas; 5, club-shaped, 2 mm in diameter and 60A in color on style arms 3 mm in length, style; 6.5 cm in length and up to 5 mm in width (at base), 46C in color and blending at base with 2C, ovary; oblong in shape with 5 pointed apex, 1.5 cm in length and 9 mm in width, 4C in color.

*Androecium*.—Stamens; average of 50, stamens are clustered and implanted into upper portion of style, anthers; dorsifixed and orbicular in shape, 1 mm in diameter, and 14C in color; filament; 5 mm in length, 0.5 mm in width, and 46A in color, pollen; abundant in quantity and 14A in color.

*Fruit/seeds*.—None observed.

It is claimed:

1. A new and distinct cultivar of *Hibiscus* plant named 'JBN 12002' as herein illustrated and described.

* * * * *